(12) United States Patent
Fujita et al.

(10) Patent No.: US 7,915,447 B2
(45) Date of Patent: Mar. 29, 2011

(54) PROCESS FOR PRODUCING SUCCINIC ACID

(75) Inventors: Ichiro Fujita, Kawasaki (JP); Kouichi Wada, Kawasaki (JP)

(73) Assignee: Showa Denko K.K., Tokyo (JP)

( * ) Notice: Subject to any disclaimer, the term of this patent is extended or adjusted under 35 U.S.C. 154(b) by 253 days.

(21) Appl. No.: 12/374,203

(22) PCT Filed: Jun. 12, 2007

(86) PCT No.: PCT/JP2007/062193
§ 371 (c)(1),
(2), (4) Date: Jan. 16, 2009

(87) PCT Pub. No.: WO2008/010373
PCT Pub. Date: Jan. 24, 2008

(65) Prior Publication Data
US 2009/0234160 A1    Sep. 17, 2009

Related U.S. Application Data

(60) Provisional application No. 60/820,621, filed on Jul. 28, 2006.

(30) Foreign Application Priority Data

Jul. 19, 2006 (JP) ................................. 2006-197233

(51) Int. Cl.
*C07C 55/10* (2006.01)
*C07C 51/42* (2006.01)
(52) U.S. Cl. ........................................ 562/590; 562/593
(58) Field of Classification Search .................. None
See application file for complete search history.

(56) References Cited

U.S. PATENT DOCUMENTS

| | | | |
|---|---|---|---|
| 5,034,105 A * | 7/1991 | Berglund et al. | 204/538 |
| 5,143,833 A | 9/1992 | Datta | |
| 5,143,834 A | 9/1992 | Glassner et al. | |
| 5,159,110 A * | 10/1992 | Thunberg | 562/554 |
| 5,168,055 A | 12/1992 | Datta et al. | |
| 5,958,744 A | 9/1999 | Berglund et al. | |
| 6,265,190 B1 | 7/2001 | Yedur et al. | |

FOREIGN PATENT DOCUMENTS

| | | |
|---|---|---|
| JP | 60-051145 A | 3/1985 |
| JP | 62-294090 A | 12/1987 |
| JP | 03-030685 A | 2/1991 |
| JP | 03-151884 A | 6/1991 |
| JP | 2944157 B2 | 6/1999 |
| JP | 2001-514900 A | 9/2001 |
| JP | 2005-333886 A | 12/2005 |
| WO | 98/01413 A | 1/1998 |
| WO | 99/09196 A1 | 2/1999 |

* cited by examiner

*Primary Examiner* — Paul A Zucker
(74) *Attorney, Agent, or Firm* — Sughrue Mion, PLLC

(57) ABSTRACT

The present invention is intended to provide a process capable of efficiently producing highly purified succinic acid from an alkali metal succinate by a simple separation and purification process. The process for producing succinic acid in the present invention comprises (1) the step to add sulfuric acid into a solution containing an alkali metal succinate, (2) the step to precipitate and remove the crystal of an alkali metal sulfate from said solution, and (3) the step to precipitate and recover the crystal of succinic acid. The removal of the crystal of an alkali metal sulfate in the step (2) is performed by a solid-liquid separation in a state that the crystal of alkali metal sulfate is precipitated by concentrating and heating the solution that is obtained by adding sulfuric acid in the step (1) and succinic acid is dissolved in the solution.

13 Claims, 5 Drawing Sheets

PROCESS FOR PRODUCING SUCCINIC ACID

CROSS REFERENCES OF RELATED APPLICATION

This application is an application filed under 35 U.S.C. §111(a) claiming benefit pursuant to 35 U.S.C. §119(e) of the filing date of Provisional Application 60/820,621 filed on Jul. 28, 2006, pursuant to 35 U.S.C. §111(b).

FIELD OF THE INVENTION

The present invention relates to a process for producing succinic acid. More particularly, it relates to a process for producing succinic acid having high purity that is useful for a polymer, a food, a medicine, and a raw material for synthesis of other chemicals by using the process in which sulfuric acid is added to a solution containing an alkali metal succinate, and then the resulting alkali metal sulfate and succinic acid are fractionally crystallized.

BACKGROUND ART

Succinic acid is widely used for a polymer, a food, a medicine, and a raw material for synthesis of other chemicals. Particularly, when it is used as a raw material for a polymer, succinic acid of high purity is required in order to maintain the degree of polymerization and prevent coloring. It is possible to obtain succinic acid of high purity by increasing the number of purification stages, but in order to perform the industrial production economically, it is necessary to simplify the steps of separation and purification.

Generally, in the production of succinic acid by a fermentation method, when the fermentation is carried out without a pH control, the produced succinic acid accumulates in the reaction system as the reaction progresses. Thereby, pH of the reaction solution is lowered and deviates from a suitable range for microorganisms to produce the succinic acid, and as a result, the rate of succinic acid production is greatly slowed. Therefore, the production rate is maintained by controlling the pH usually by adding an alkaline material. Thus, an alkali-metal succinate is a form commonly observed in the reaction solution for producing succinic acid by a fermentation method.

As a method for producing succinic acid of high purity from a reaction solution containing an alkali metal succinate, the method to change an unsaturated aqueous solution of the salt of succinic acid into a supersaturated aqueous solution of free succinic acid by a water-splitting electrodialysis followed by crystallization from the said supersaturated aqueous solution of succinic acid is known (see Patent Document 1).

The method in Patent Document 1, however, has a problem that, in the processes of separation and purification of succinic acid, there are too many steps because it requires an ordinary electrodialysis and the like prior to the step of the water-splitting electrodialysis in order to obtain the supersaturated aqueous solution. In addition, there is a problem, in the case of performing an industrial production by using the electrodialysis, that not only the initial investment cost for the purchase of equipments but also the running costs after the operation, such as use of a cleaning agent for an electrodialysis membrane, exchange of a deteriorated membrane and the like, are high.

As an alternative method, a process that involves the following steps is known; $Ca(OH)_2$ is added to transform to Ca succinate, which is then recovered as crystals. Thereafter, calcium is precipitated as gypsum by adding sulfuric acid while succinic acid is recovered as a solution, and then succinic acid is crystallized by cooling (see Patent Document 2). However, the method of Patent Document 2 has a problem that there are too many steps and alkaline wastewater is produced at the time of recovering Ca succinate.

In addition, as an alternative method, a process that involves the following steps is known; ammonium sulfate is added under acidic condition, then succinic acid is recovered by salting-out. Thereafter, remaining ammonium sulfate is removed by extracting with methanol, and then the solvent is recovered to crystallize succinic acid (Patent Document 3). However, the method of Patent Document 3 has a problem that, because it involves treatments in the system of two liquid phases of water and methanol, not only the number of steps is increased, but also equipments durable for an organic solvent are needed.

For the reasons as mentioned above, it has been desired to establish the efficient production process that involves less steps, versatile equipments with low running costs, and simple steps of separation and purification.

[Patent Document 1] Japanese Patent No. 2944157
[Patent Document 2] Japanese Patent Laid-Open Publication No. S62-294090
[Patent Document 3] Japanese Patent Application Laid-Open No. 2001-514900

DISCLOSURE OF THE INVENTION

Problems to be Solved by the Invention

An object of the present invention is to provide a process to efficiently produce highly-purified succinic acid from an alkali metal succinate by simple separation and purification processes.

Means to Solve the Problems

The present inventors carried out an extensive study to address the above-mentioned problems. As a result, the present inventors found that succinic acid of high purity could be separated and purified in a simple and efficient manner from a solution containing an alkali metal succinate salt by adding sulfuric acid into the solution containing the alkali metal succinate, then fractionally crystallizing the resulting alkali metal sulfate and succinic acid in a state that the alkali metal sulfate salt and succinic acid coexist, and thus completed the present invention.

Namely, the present invention is a method to produce succinic acid by performing a two-stage crystallization that involves the following processes: sulfuric acid is added into the solution containing the alkali metal succinate to set the state that the alkali metal sulfate and succinic acid coexist; then firstly the crystal of alkali metal sulfate is selectively precipitated and removed; and subsequently the crystal of succinic acid is selectively precipitated and recovered.

Further, the present invention comprises, for instance, the following processes:

[1] A process for producing succinic acid, including (1) a step to add sulfuric acid into a solution containing an alkali metal succinate, (2) a step to precipitate and remove the crystal of the alkali metal sulfate from the solution, and (3) a step to precipitate and recover the crystal of succinic acid;

[2] The process for producing succinic acid according to the above [1], wherein an amount of sulfuric acid to be added in the step (1) corresponds to the equivalent amount of the alkali metal contained in the solution;

[3] The process for producing succinic acid according to the above [1], wherein the removal of the crystal of the alkali metal sulfate in the step (2) is performed by a solid-liquid separation in a state that the crystal of the alkali metal sulfate is precipitated by concentrating and beating the solution that is obtained by adding sulfuric acid in the step (1) and succinic acid is dissolved in the solution;

[4] The process for producing succinic acid according to the above [3], wherein the concentration of the alkali metal sulfate is 20 g/100 g-water or more and the concentration of succinic acid is 60 g/100 g-water or less in the solution that is obtained by concentrating and heating the reaction solution added with sulfuric acid, and temperature of the heating is 50° C. or higher.

[5] The process for producing succinic acid according to any of the above [1] to [4], wherein the recovery of the crystal of succinic acid in the step (3) is performed by a solid-liquid separation in a state that succinic acid is crystallized by cooling the solution that is obtained after removing the crystal of the alkali metal sulfate, and the unremoved alkali metal sulfate that is remained in the step (2) is dissolved in the solution;

[6] The process for producing succinic acid according to the above [5], wherein the cooling temperature of the solution that is obtained after removing the crystal of the alkali metal sulfate is 50° C. or lower;

[7] The process for producing succinic acid according to the above [5] or [6], further comprising a step to rinse the recovered crystal of succinic acid by water, the temperature of which is lower than the temperature employed for cooling the solution that is obtained after removing the alkali metal sulfate;

[8] The process for producing succinic acid according to the above [5] or [6], further comprising the step in which the recovered crystal of succinic acid is re-dissolved into water, and then succinic acid is re-crystallized by cooling and recovered;

[9] The process for producing succinic acid according to the above [8], further comprising a step to treat the solution in which the crystal of succinic acid is re-dissolved with activated carbons after the crystal of succinic acid is re-dissolved into water and before the recovery of succinic acid by re-crystallization;

[10] The process for producing succinic acid according to the above [3], wherein the remaining solution after recovering the crystal of succinic acid is reprocessed by mixing it with the solution before the concentration and heating in the step (2);

[11] The process for producing succinic acid according to the above [3], wherein the rinse water recovered after rinsing the crystal of succinic acid is reprocessed by mixing it with the solution before the concentration and heating in the step (2);

[12] The process for producing succinic acid according to the above [1], wherein the solution containing the alkali metal succinate is a broth by microorganisms;

[13] The process for producing succinic acid according to the above [1], wherein the solvent of the solution that contains the alkali metal succinate is water.

Effects of the Invention

By using the production processes of the present invention, succinic acid of high purity can be efficiently produced.

BEST MODE FOR CARRYING OUT THE INVENTION

Figure 1:
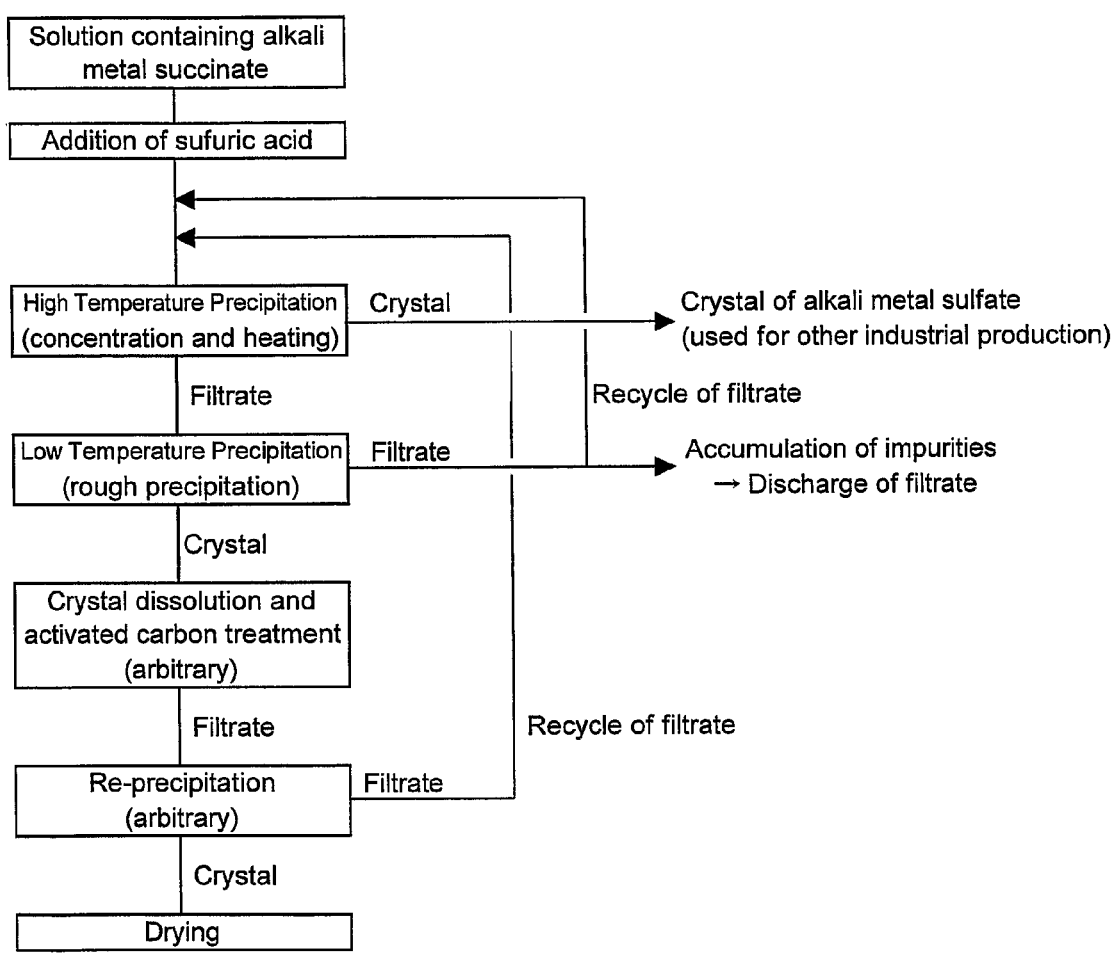
FIG. 1 This Figure is a flow chart showing the process for producing succinic acid of the present invention.

The process for producing succinic acid related to the present invention will be explained in detail as follows. Here, FIG. 1 shows the flow chart of the production steps of succinic acid in the present invention.

<Preparation of the Solution Containing an Alkali Metal Succinate Salt>

In the present invention, a solution containing an alkali metal succinate is used as the starting raw material. The solution is not particularly restricted so long as it contains an alkali metal succinate, and a kind of the salt is not particularly restricted so long as it is a salt of an alkali metal. The solvent is preferably water that contains no organic solvent.

Examples of the solution that contains the alkali metal succinate include, a reaction solution of the alkali metal succinate salt produced by fermentation by microorganisms. The reaction solution of an alkali metal salt obtained by use of microorganisms may be obtained, for instance, by cultivating the microorganisms capable of producing succinic acid in a culture medium that contains a carbon source, a nitrogen source, and the like with adding an aqueous solution of an alkali metal hydroxide as a pH adjusting agent into it. In this reaction solution, there may be contained a small amount of other organic acids such as acetic acid, lactic acid and the like as by-products of fermentation, and their metal salts.

In the present invention, the alkali metal succinate can be converted into the free succinic acid by the two-stage crystallization as follows: sulfuric acid is added into the solution that contains the alkali metal succinate to set a state that the alkali metal sulfate and succinic acid coexist; then firstly the crystal of the alkali metal sulfate is selectively precipitated and removed, and thereafter, the crystal of succinic acid is selectively precipitated and recovered. Further, the acid-converted succinic acid is re-dissolved into water, and then the crystal is recovered by re-crystallization by cooling the solution to obtain succinic acid of high purity.

<Addition of Sulfuric Acid>

The purpose of the addition of sulfuric acid into the solution containing the alkali metal succinate salt is to make an alkali metal sulfate by charging the sulfate ion as the counter ion of an alkali metal ion in the solution, and to precipitate the alkali metal sulfate to the maximum extent for its removal in the subsequent step of crystallization of the alkali metal sulfate (hereinafter this step may be also called "High Temperature Crystallization"). However, the addition of sulfuric acid to an alkali metal leaves the sulfate as the impurity, which causes a problem for the recovery of succinic acid of high purity. For this reason, the amount of sulfuric acid to be added into the reaction solution preferably corresponds to the equivalent amount of the alkali metal that is contained in the reaction solution.

As mentioned above, in the fermentation liquor produced by microorganism, other organic acids usually coexist along with succinic acid as by-products. Accordingly, an alkali metal hydroxide to be added at the reaction is to neutralize not only succinic acid but also other organic acids. Thus, the equivalent amount of succinic acid contained in the solution is not necessarily the same as the equivalent amount of alkali metal. Namely, in order to obtain the accurate amount of the sulfuric acid to be added, it is preferred to use the equivalent amount of the alkali metal rather than the equivalent amount of succinic acid.

<High Temperature Crystallization>

The solution obtained after adding sulfuric acid is concentrated and heated in such a manner as to give the solution in which the concentration of the alkali metal sulfate is more than its saturation solubility in the solution and that of succinic acid is less than its saturation solubility in the solution, so that the crystal of the alkali metal sulfate is precipitated selectively. The concentration of the alkali metal sulfate after concentration and heating, the concentration of succinic acid, and the temperature are not particularly restricted, so long as they satisfy the above-mentioned conditions and the selective crystallization of the crystal of the alkali metal sulfate is not adversely affected.

In the system in which succinic acid and the alkali metal salt coexist, the solubility of succinic acid tends to increase as the temperature increases, while the solubility of the alkali metal salt tends to decrease or stay nearly constant as the temperature increases. Therefore, in order to further increase the recovered amount of succinic acid and to further decrease the amount of alkali metal salts that will become impurities in performing the selective crystallization and recovery of succinic acid in the subsequent step (hereinafter, this step may be also called "Low Temperature Crystallization"), it is preferred that the temperature after concentration and heating is as high as possible so long as the decomposition of succinic acid does not take place, usually 50° C. or higher, more preferably 70 to 80° C.

Further, as for the concentrations of the alkali metal sulfate and succinic acid after the concentration and heating, for instance when the heating temperature is set at 50° C. or higher, it is preferred that the concentration of the alkali metal sulfate in the solution is 20 g/100 g-water or higher and the concentration of succinic acid is 60 g/100 g-water or lower, and more preferably, the concentration of the alkali metal sulfate is in the range of 60 to 80 g/100 g-water and the concentration of succinic acid is in the range of 30 to 50 g/100 g-water.

When the concentrations are outside the above-mentioned ranges, for instance, when the concentration of succinic acid is above the range, succinic acid is precipitated along with the alkali metal sulfate, and thus it leads to the loss of succinic acid. Also, when the concentration of succinic acid is below the range, the recovery yield of the crystal of succinic acid tends to be lowered in the subsequent step, namely, the process of Low Temperature Crystallization. On the contrary, when the concentration of the alkali metal sulfate is above the range, the amount of its crystal is so large that the efficiency of the solid-liquid separation tends to be lowered. Also, when the concentration of the alkali metal sulfate is below the range, the amount of its crystal is lowered and the ratio of the amount of the crystal of the alkali metal sulfate to the total amount is lowered so that the removal efficiency tends to be decreased.

As the solid-liquid separation methods for the precipitated alkali metal sulfate, such methods as a centrifugal separation, a centrifugal filtration, a filter press, a membrane filtration and the like may be employed, that have the function to maintain the temperature in the systems during the solid-liquid separation at the same level or above of the temperature at the concentration and heating, and keep a state that only the crystal of the alkali metal sulfate is precipitated while the crystal of succinic acid is not precipitated during the separation process.

<Low Temperature Crystallization>

A state is set in such a manner that the crystal of succinic acid are selectively precipitated by cooling the above-mentioned solution obtained after removing the crystal of the alkali metal sulfate.

In the cooled solution, uncrystallized succinic acid and the remaining alkali metal sulfate that is not crystallized in the previous step are dissolved. Therefore, in order to make a state that the alkali metal sulfate is more surely dissolved, the concentration of the alkali metal sulfate may be lowered by cooling and diluting with water at the same time.

Although the temperature for cooling is not particularly restricted so long as the selective crystallization of succinic acid is not adversely affected, the temperature is preferred to be lower than that in the process of the High Temperature Crystallization, namely 50° C. or lower, and more preferably 35 to 40° C.

Figure 2:
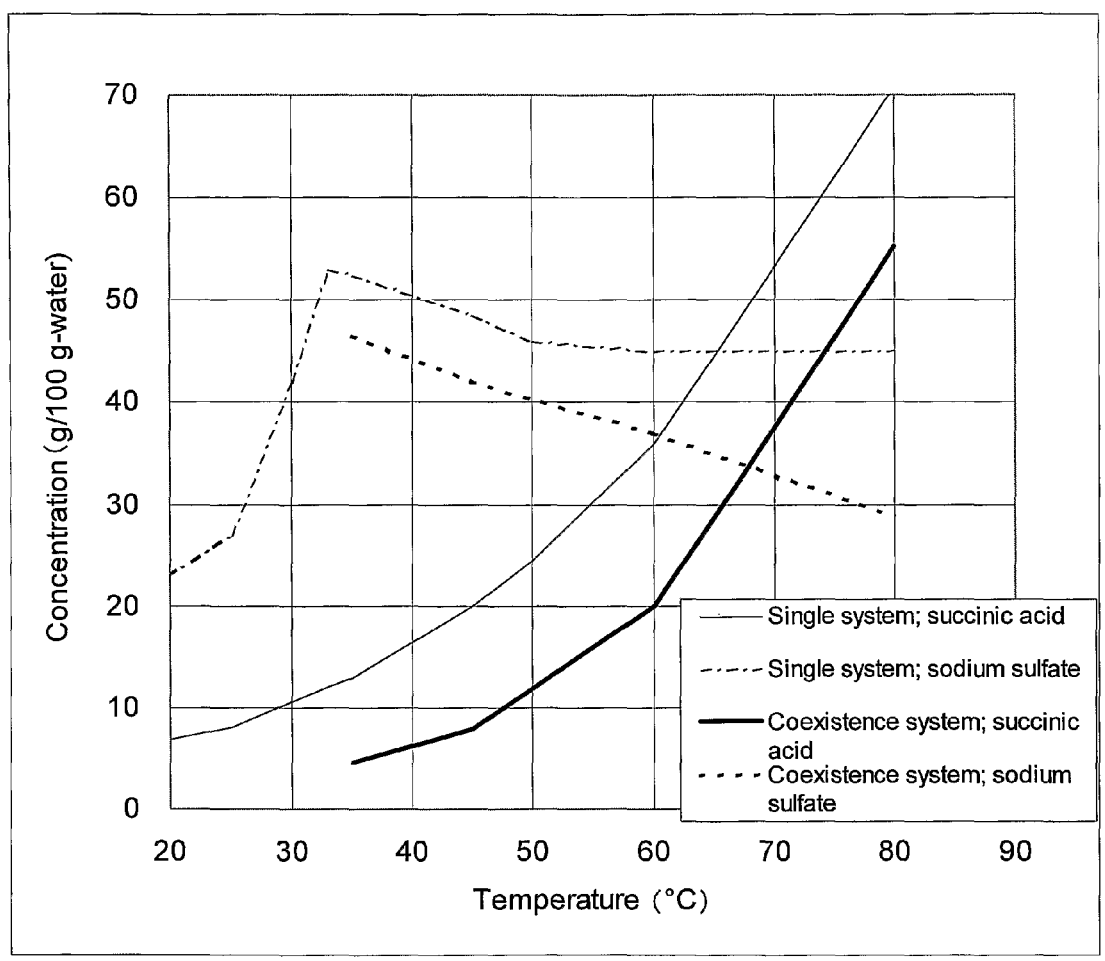
FIG. 2 This Figure shows the saturation solubility curves of succinic acid and sodium sulfate relative to water by using the model solutions.

As the alkali metal sulfate, there may be mentioned sodium sulfate and potassium sulfate, but sodium sulfate is particularly preferred. The saturation solubility of sodium sulfate in water is almost constant above the transition temperature from the crystal water type to the anhydrous salt type. On the other hand, the saturation solubility of succinic acid in water is increased as the temperature becomes higher. Therefore, the saturation solubility curves for the both compounds intersect with each other as shown in FIG. 2. It is possible to selectively precipitate sodium sulfate at the temperature region higher than the intersected temperature, and it is possible to selectively precipitate succinic acid at the temperature region lower than the intersected temperature. Meanwhile, it is preferred to selectively crystallize the compounds at the temperature where the difference in the saturation solubility of the two compounds is large. Further as shown in FIG. 2, the precipitation of sodium sulfate takes place easily at the temperature lower than the transition temperature from the crystal water type to the anhydrous salt type (32.4° C.) as the saturation solubility of sodium sulfate is lowered. For this reason, it is preferred to perform the Low Temperature Crystallization at 35° C. or higher.

Recovery of the crystal is performed by solid-liquid separation of the solution containing crystallized succinic acid (hereinafter this solution may be also called "Crystal Solution") followed by rinsing to remove impurities attached to the crystal.

As the methods for solid-liquid separation, such methods as a centrifugal separation, a centrifugal filtration, a filter press filtration, a membrane filtration and the like may be employed. In terms of the recovery efficiency of succinic acid and the removal efficiency of attached impurities, the solid-liquid separation method with a filter cloth type is advantageous. In particular, it is preferred to employ a filter press and/or a centrifugal filtration. In addition, in terms of maintaining the crystal recovery yield, it is preferred to maintain the temperature of the Crystal Solution at the temperature employed during the cooling.

Further, the impurities attached to the crystal can be rinsed out by charging water or the filtrated solution that is recovered after solid-liquid separation in the re-crystallization process described below, as a rinsing solution, onto the filtration surface in a state that the crystal in the Crystal Solution is recovered on the filtration surface in the solid-liquid separation process. It is preferred that the rinsing solution is cooled below the temperature of the Crystal Solution in terms of securing the yield of crystal recovery. In addition, it is preferred that the concentration of succinic acid in the rinsing solution is near the concentration of the saturation solubility at the temperature to minimize the loss of succinic acid caused by dissolution into the rinsing solution. For example, when water is used as the rinsing solution, it is preferred to lower the saturation solubility by lowering the water temperature. The amount of charging liquid can be adjusted appropriately depending on the kinds and amounts of impurities in the filtrated solution, intended purity level, recovery yield, and the like.

<Dissolution of Crystal, Treatment with Activated Carbons, and Re-Crystallization>

In the solid-liquid separation process for recovery of the succinic acid crystal, if it is desired to further reduce the concentration of impurities attached to the crystal, the attached impurities can be removed by the following processes: after the recovered succinic acid crystal is dissolved in water or hot water, the obtained solution is treated with activated carbons as necessary, and is cooled to re-precipitate the crystal, which is again separated by solid-liquid separation.

In this case, the concentration of succinic acid after dissolution and the cooling temperature are not particularly restricted so long as they do not adversely affect the crystallization by cooling. Further, the process of solid-liquid separation may be performed only by the recovery of the crystal, and also the crystal may be rinsed as necessary by charging water after the solid-liquid separation. In addition, the number of operation for re-precipitation and solid-liquid separation is not necessarily limited to one time <Drying>

The recovered crystal of succinic acid can be dried by removal of water to make a dry product. The methods for drying in the present case are not particularly restricted so long as the drying is performed so that the properties of succinic acid would not change and that succinic acid would not be contaminated by impurities.

Meanwhile, the residual solution that is obtained after recovering succinic acid crystal by Low Temperature Crystallization and re-crystallization can be reprocessed by putting back to the solution before the concentration and heating process. When the reprocessing is performed, since impurities in the system are accumulated, it is preferred that the filtrated solution of the Low Temperature Crystallization is removed outside the system without being reprocessed appropriately in view of the efficiency of separation and purification.

As explained in the above, the process for producing succinic acid of the present invention is the process in which sulfuric acid is added into the solution containing the alkali metal succinate, and then the alkali metal sulfate and succinic acid are fractionally crystallized in a state that the alkali metal sulfate and succinic acid coexist, which is a simple purification process involving only a crystallization technique with less steps. By the production process of the present invention, it is possible to obtain the crystal of succinic acid with high purity in an efficient manner by using versatile equipments for performing a crystallization process.

EXAMPLES

In the following, the present invention will be explained more specifically based on examples, but the present invention is not restricted by these examples at all. Meanwhile, in the following examples, a certain amount of materials are lost due to sampling for analyses of components in each step, but the yield and the like were recorded without taking these losses into consideration.

<Measurement of the Eutectic Point by Using a Model Solution>

Figure 3:
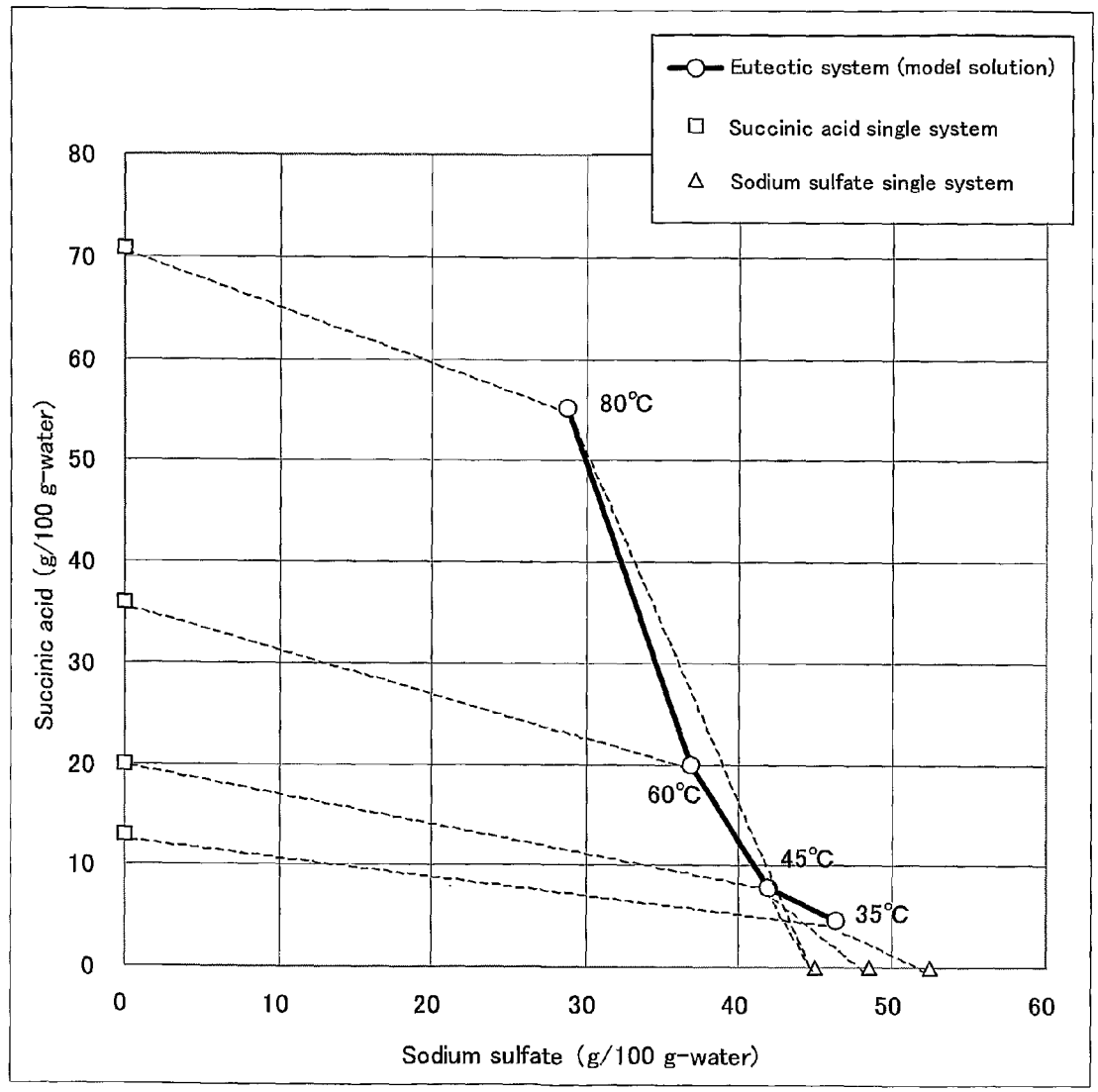
FIG. 3 This Figure shows the eutectic diagram of succinic acid and sodium sulfate in the model solutions.

To 180 g of water in a 500 mL-Erlenmeyer flask with a stopper were added 144 g of succinic acid and 108 g of sodium sulfate to prepare the supersaturated coexistence slurry solution. The slurry solution was kept in a water bath with stirring and adjusted at 35° C., 45° C., 60° C., and 80° C., respectively, followed by stirring for 2 hours or longer after they reached their intended temperatures. After that, the concentrations of succinic acid and sodium sulfate in the supernatant were analyzed. As a result, the concentrations of succinic acid were 4.6 g/100 g-water at 35° C., 7.8 g/100 g-water at 45° C., 20.0 g/100 g-water at 60° C., and 55.3 g/100 g-water at 80° C., respectively. And the concentrations of sodium sulfate were 46.4 g/100 g-water at 35° C., 42.0 g/100 g-water at 45° C., 36.9 g/100 g-water at 60° C., and 28.8 g/100 g-water at 80° C., respectively. The solubility curves of these compounds are shown in FIG. 2 (see coexistence system), and the eutectic lines are shown in FIG. 3. Here, "g/100 g-water" means the concentration unit as expressed in terms of weight (g) of the solute dissolved in 100 g of water.

From FIG. 2, a tendency can be seen that, in the model system of two components containing succinic acid and sodium sulfate, as the temperature is lowered, the solubility of succinic acid is decreased while the solubility of sodium sulfate is increased, and as the temperature is raised, the solubility of succinic acid is increased while the solubility of sodium sulfate is decreased. Thus it was confirmed that sodium sulfate could be selectively precipitated at higher temperature region, or succinic acid could be selectively precipitated at lower temperature region.

In addition, it was found that the eutectic lines tend to tilt slightly toward the left side as shown in FIG. 3. It was confirmed that, in the coexistence solution having the composition of succinic acid and sodium sulfate in the lower left region from the eutectic line, in the case that the moving line of the concentration with a constant ratio of the two components intersects with the eutectic line when the coexistence solution was concentrated, a state in which sodium sulfate was selectively crystallized could be obtained when the coexistence solution was concentrated by choosing the temperature of the coexistence solution above the temperature of the intersected eutectic point, and furthermore, a state in which succinic acid was selectively crystallized could be obtained on cooling after the precipitated sodium sulfate was removed.

<Addition of Sulfuric Acid to the Reaction Solution and Measurement of Eutectic Point>

Figure 4:
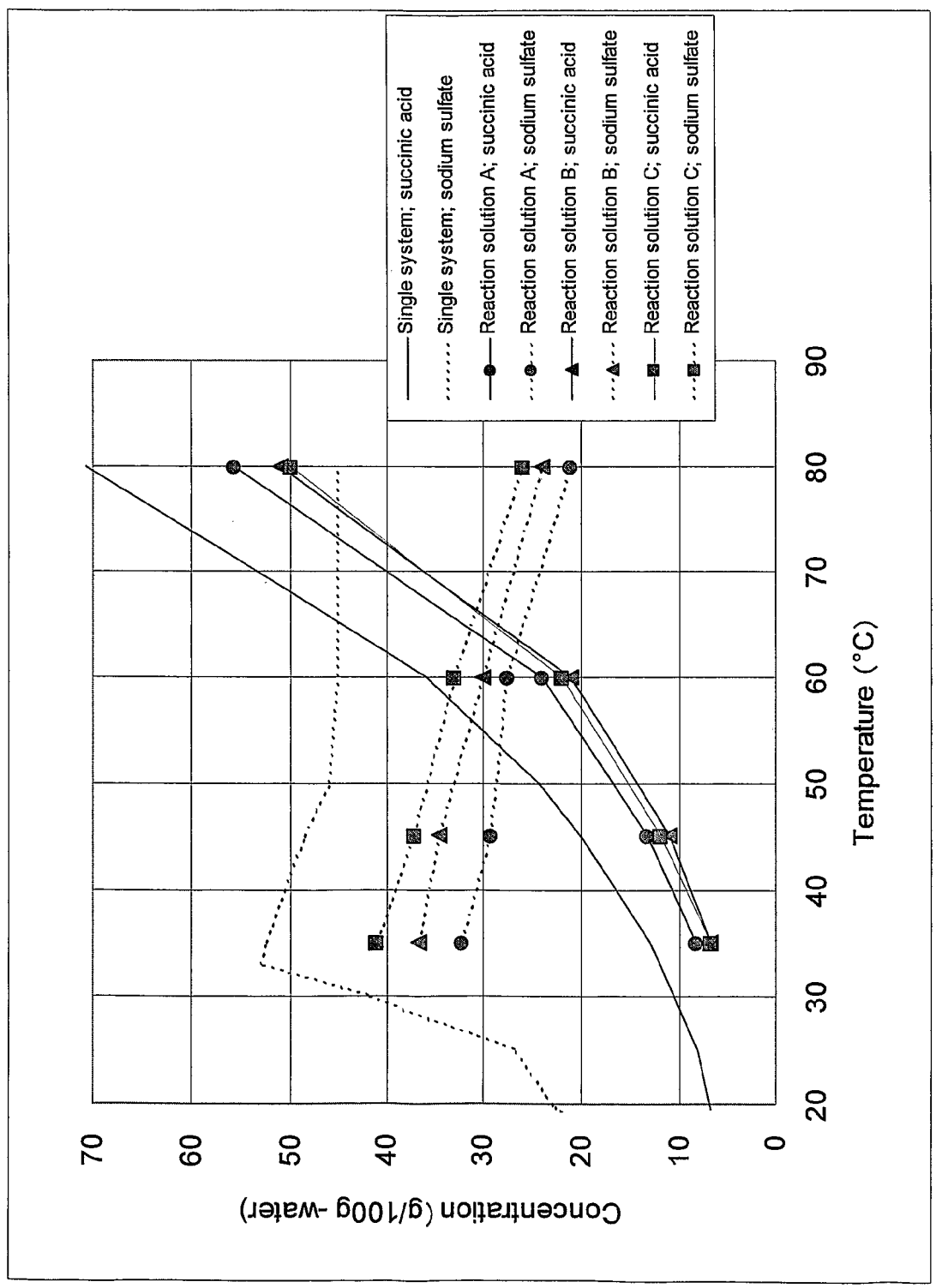
FIG. 4 This Figure shows the saturation solubility curves of Succinic acid and sodium sulfate relative to water in the reaction solution.
Figure 5:
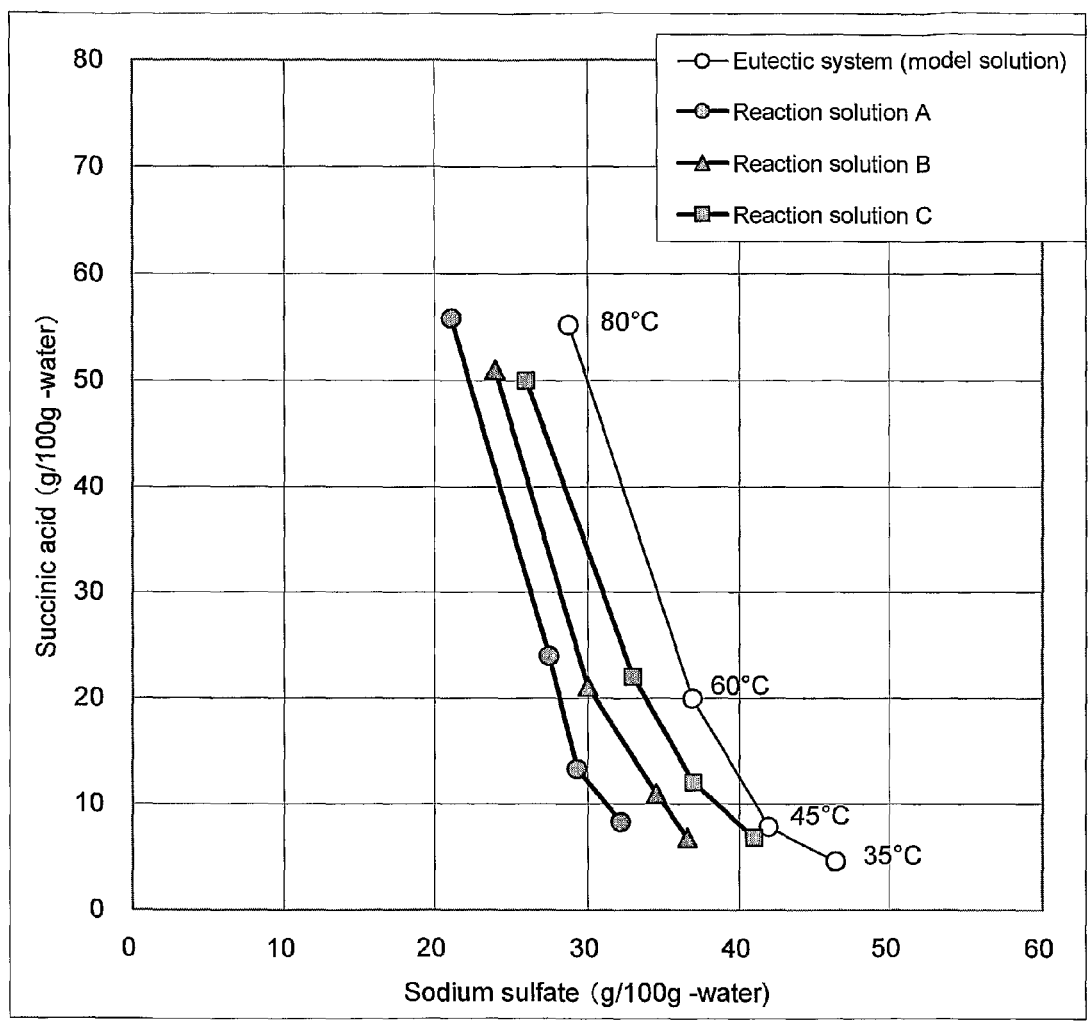
FIG. 5 This Figure shows the eutectic lines of succinic acid and sodium sulfate in the reaction solution.

The sterile reaction solutions (A), (B) and (C) of 1.0 L each, having the composition of an organic acid, a cation, an anion, and sugar, as determined by HPLC analysis shown in Table 1 and containing Na succinate produced by fermentation, were taken in beakers. Then, sulfuric acid was added into them in such amounts as to give the same equivalent amount as the concentrations of the alkali metals contained in the respective solutions, namely 111 g of sulfuric acid to the reaction solution (A), 84 g of sulfuric acid to the reaction solution (B), and 50 g of sulfuric acid to the reaction solution (C), with stirring the solutions by stirrers. These solutions were concentrated with a rotary evaporator by five folds to attain the supersaturated state, and then all of the slurry solutions were transferred into a 300 mL-Erlenmeyer flask with a stopper. These were stirred by stirrers in water baths to adjust their temperatures at 35° C., 45° C., 60° C. and 80° C. Then the concentrations of succinic acid and sodium sulfate in the supernatants were measured after stirring two hours or longer after they reached the temperatures, and the solubility curves (FIG. 4) and the eutectic lines (FIG. 5) were confirmed.

It was confirmed that the solubility curves and the eutectic lines of the reaction solutions were similar to those of the model solutions, and therefore the fractional crystallizations as mentioned above were possible.

Example 1

Separation and Purification of the Reaction Solution (A)

(Addition of Sulfuric Acid)

To 2080 g (2.0 L) of the reaction solution (A) having the composition as shown in Table 1, 223 g of concentrated sulfuric acid that corresponds to the equivalent amount of the alkali metals contained in the reaction solution (A) was added with stirring to obtain the initial process solution. As shown in Table 2, the initial process solution contained 2303 g (2.2 L) of the reaction solution, containing 231 g (13.7 g/100 g-water) of succinic acid and 323 g (19.2 g/100 g-water) of sodium sulfate.

(High Temperature Crystallization)

Subsequently, the initial process solution was concentrated with a rotary evaporator to be 1082 g to make the concentration of succinic acid 46 g/100 g-water and sodium sulfate 65 g/100 g-water, and then all of the solution was transferred into an Erlenmeyer flask with a stopper. The flask was plugged with a stopper and then the solution in the flask was warmed with stirring in a water bath at 80° C. in the hermetically closed state. After the concentrated solution was stirred at 80° C. for 2 hours, solid-liquid separation was performed by a suction filtration using a 5B filter paper and a Nutsche funnel having an inner diameter of 110 mm which was warmed at 80° C. in advance.

The weight of recovered filtrated solution was 798 g, containing 215 g of succinic acid, 77 g of sodium sulfate, 483 g of water, and 22 g of other components. Also, the weight of recovered crystal was 284 g, containing 245 g of sodium sulfate, 16 g of succinic acid, 17 g of water, and 5 g of other components. By the High Temperature Crystallization, 93% of succinic acid in the initial process solution was recovered in the filtrated solution, while 76% of sodium sulfate in the initial process solution was removed as the crystal.

(Low Temperature Crystallization)

All of 798 g of the filtrated solution recovered by the High Temperature Crystallization was transferred into an Erlenmeyer flask with a stopper. The flask was plugged with a stopper and then the solution in the flask was cooled with stirring in a water bath at 35° C. in the hermetically closed state. After the concentrated solution was stirred at 35° C. for 2 hours, solid-liquid separation was performed by a suction filtration using a 5B filter paper and a Nutsche funnel having an inner diameter of 110 mm which was kept at 35° C. in advance. Further, after all of the crystals were recovered on the funnel, the crystals on the funnel were rinsed by charging 215 g of water with a temperature of 35° C.

The weight of the recovered crystal was 176 g, containing 164 g of succinic acid, 0 g of sodium sulfate, 10 g of water, and 2 g of other components. Also, the weight of the recovered filtrated solution including the rinse water was 837 g in total, containing 51 g of succinic acid, 77 g of sodium sulfate, 688 g of water, and 20 g of other components. By the Low Temperature Crystallization, 71% of succinic acid was recovered as the crystal relative to 100% of succinic acid contained in the initial process solution, while 24% of sodium sulfate was contained in the filtrated solution and was removed. In addition, in the recovered succinic acid crystal, Na was completely removed, and furthermore impurities such as organic acids other than succinic acid and the like were removed by 97%.

(Re-Crystallization)

In Order to Remove Other Components Contained in the recovered crystal by the Low Temperature Crystallization, 176 g of the crystal recovered by the Low Temperature Crystallization was added to 650 g of water in an Erlenmeyer flask with a stopper with stirring. Then, the flask was plugged with a stopper, and the solution in the flask was warmed with stirring in a water bath at 65° C. in the hermetically closed state. Warming at 65° C. and stirring by a stirrer were continued, and when it was confirmed that the crystals were completely dissolved, the solution in the flask was cooled to 5° C. with stirring in a water bath. After the filtrated solution was stirred with maintaining the temperature at 5° C. for 2 hours, solid-liquid separation was performed by a suction filtration using a 5B filter paper and a Nutsche funnel having an inner diameter of 110 mm which was cooled at 5° C. in advance. Further, after all of the crystals were recovered on the funnel, the crystals on the funnel were rinsed by charging 160 g of water with a temperature of 5° C.

The weight of the recovered crystal was 152 g, containing 140 g of succinic acid, 0 g of sodium sulfate, 12 g of water, and 0 g of other components. Also, the weight of the recovered filtrated solution including the rinse water was 834 g, containing 24 g of succinic acid, 0 g of sodium sulfate, 808 g of water, and 2 g of other components. By re-crystallization, 61% of succinic acid was recovered as the crystal relative to 100% of succinic acid contained in the initial process solution. In addition, impurities were completely removed from the recovered crystal of succinic acid. When the filtrated solution recovered in the processes of the Low Temperature Crystallization and the re-crystallization were recycled to the subsequent treatments, the amount of the loss of succinic acid that cannot be recycled in this Example was 16 g, namely 7% relative to its content in the initial process solution.

Example 2

Separation and Purification of the Reaction Solution (B)

(Addition of Sulfuric Acid)

To 2060 g (2.0 L) of the reaction solution (B) having the composition as shown in Table 1, 168 g of concentrated sulfuric acid that corresponds to the equivalent amount of the alkali metals contained in the reaction solution was added with stirring to obtain the initial process solution. As shown in Table 2, the initial process solution contained 2228 g (2.1 L) of the reaction solution, containing 161 g (9.3 g/100 g-water) of succinic acid and 244 g (14.0 g/100 g-water) of sodium sulfate.

(High Temperature Crystallization)

Subsequently, the initial process solution was concentrated with a rotary evaporator to be 795 g to make the concentration of succinic acid 46 g/100 g-water and sodium sulfate 69 g/100 g-water, and then all of the solution was transferred into an Erlenmeyer flask with a stopper. The flask was plugged with a stopper and then the solution in the flask was warmed with stirring in a water bath at 80° C. in the hermetically closed state. After the concentrated solution was stirred at 80° C. for 2 hours, solid-liquid separation was performed by a suction filtration using a 5B filter paper and a Nutsche funnel having an inner diameter of 110 mm which was warmed at 80° C. in advance.

The weight of recovered filtrated solution was 577 g, containing 152 g of succinic acid, 58 g of sodium sulfate, 338 g of water, and 29 g of other components. Also, the weight of the recovered crystal was 218 g, containing 185 g of sodium sulfate, 10 g of succinic acid, 17 g of water, and 6 g of other components. By the High Temperature Crystallization, 94% of succinic acid in the initial process solution was recovered in the filtrated solution, and 76% of sodium sulfate in the initial process solution was removed as the crystal.

(Low Temperature Crystallization)

All of 577 g of the filtrated solution recovered by the High Temperature Crystallization was transferred into an Erlenmeyer flask with a stopper. The flask was plugged with a stopper and then the solution in the flask was cooled with stirring in a water bath at 35° C. in the hermetically closed state. After the concentrated solution was stirred at 35° C. for 2 hours, solid-liquid separation was performed by a suction filtration using a 5B filter paper and a Nutsche funnel having an inner diameter of 110 mm which was kept at 35° C. in advance. Further, after all of the crystals were recovered on the funnel, the crystals on the funnel were rinsed by charging 152 g of water with a temperature of 35° C.

The weight of the recovered crystal was 125 g, containing 113 g of succinic acid, 0 g of sodium sulfate, 10 g of water, and 2 g of other components. Also, the weight of the recovered filtrated solution including the rinse water was 604 g in total, containing 39 g of succinic acid, 58 g of sodium sulfate, 480 g of water, and 27 g of other components. By the Low Temperature Crystallization, 70% of succinic acid was recovered as the crystal relative to 10% of succinic acid contained in the initial process solution, while 24% of sodium sulfate was contained in the filtrated solution and was removed. In addition, in the recovered succinic acid crystal, Na was completely removed, and furthermore other impurities were removed by 97%.

(Re-Crystallization)

In order to remove other components contained in the recovered crystal by the Low Temperature Crystallization, 125 g of the crystal recovered by the Low Temperature Crystallization was added to 450 g of water in an Erlenmeyer flask with a stopper with stirring. Then, the flask was plugged with a stopper, and the solution in the flask was warmed with stirring in a water bath at 65° C. in the hermetically closed state.

Warming at 65° C. and stirring by a stirrer were continued, and when it was confirmed that the crystals were completely dissolved, 3.4 g of activated carbons BA-50 (manufactured by Ajinomoto-Fine-Techno Co., Inc.), 3% relative to the weight of succinic acid, was added. The treatment by warming at 65° C. and stirring was continued for 1 hour after adding the activated carbons, the filtrated solution was recovered by a suction filtration using a 5C filter paper and a Nutsche funnel having an inner diameter of 110 mm which was kept at 65° C. in advance. The weight of the recovered filtrated solution was 550 g, and 109 g of succinic acid was contained in it.

All of the recovered filtrated solution was transferred into an Erlenmeyer flask with a stopper, and the solution in the flask was cooled with stirring in a water bath at 5° C. in the hermetically closed state. After the filtrated solution was stirred with maintaining the temperature at 5° C. for 2 hours, solid-liquid separation was performed by a suction filtration using a 5B filter paper and a Nutsche funnel having an inner diameter of 110 mm which was kept at 5° C. in advance. Further, after all of the crystals were recovered on the funnel, the crystals on the funnel were rinsed by charging 110 g of water with a temperature of 5° C.

The weight of the recovered crystal was 97 g, containing 90 g of succinic acid, 0 g of sodium sulfate, 7 g of water, and 0 g of other components. Also, the weight of the recovered filtrated solution including the rinse water was 563 g in total, containing 19 g of succinic acid, 0 g of sodium sulfate, 543 g of water, and 1 g of other components. By re-crystallization, 56% of succinic acid was recovered as the crystal relative to 100% of succinic acid contained in the initial process solution. In addition, impurities were completely removed from the recovered crystal of succinic acid. When the filtrated solutions recovered in the processes of the Low Temperature Crystallization and the re-crystallization were recycled to the subsequent treatments, the amount of the loss of succinic acid that cannot be recycled in this Example was 14 g, 9% relative to its content in the initial process solution.

Example 3

Separation and Purification of the Reaction Solution C (Addition of Sulfuric Acid)

To 2040 g (2.0 L) of the reaction solution (C) having the composition as shown in Table 1, 100 g of concentrated sulfuric acid was added with stirring to obtain the initial process solution. As shown in Table 2, the initial process solution contained 2140 g (2.1 L) of the reaction solution, containing 72 g (4.0 g/100 g-water) of succinic acid and 145 g (7.9 g/100 g-water) of sodium sulfate.

(High Temperature Crystallization)

Subsequently, the initial process solution was concentrated with a rotary evaporator to be 456 g to make the concentration of succinic acid 36 g/100 g-water and sodium sulfate 73 g/100 g-water, and then all of the solution was transferred into an Erlenmeyer flask with a stopper. The flask was plugged with a stopper and then the solution in the flask was warmed with stirring in a water bath at 80° C. in the hermetically closed state. After the concentrated solution was stirred at 80° C. for 2 hours, solid-liquid separation was performed by a suction filtration using a 5B filter paper and a Nutsche funnel having an inner diameter of 110 mm which was warmed at 80° C. in advance.

The weight of the recovered filtrated solution was 324 g, containing 66 g of succinic acid, 33 g of sodium sulfate, 190 g of water, and 35 g of other components. Also, the weight of the recovered crystal was 132 g, containing 112 g of sodium sulfate, 7 g of succinic acid, 10 g of water, and 4 g of other components. By the High Temperature Crystallization, 91% of succinic acid in the initial process solution was recovered in the filtrated solution, and 77% of sodium sulfate was removed as the crystal.

(Low Temperature Crystallization)

All of 324 g of the filtrated solution recovered by the High Temperature Crystallization was transferred into an Erlenmeyer flask with a stopper. The flask was plugged with a stopper and then the solution in the flask was cooled with stirring in a water bath at 35° C. in the hermetically closed state. After the concentrated solution was stirred at 35° C. for 2 hours, solid-liquid separation was performed by a suction filtration using a 5B filter paper and a Nutsche funnel having an inner diameter of 110 mm which was kept at 35° C. in advance. Further, after all of the crystals were recovered on the funnel, the crystals on the funnel were rinsed by charging 66 g of water with a temperature of 35° C.

The weight of the recovered crystal was 59 g, containing 51 g of succinic acid, 0 g of sodium sulfate, 5 g of water, and 3 g of other components. Also, the weight of the recovered filtrated solution including the rinse water was 331 g in total, containing 15 g of succinic acid, 33 g of sodium sulfate, 251 g of water, and 32 g of other components. By the Low Temperature Crystallization, 70% of succinic acid was recovered as the crystal relative to 100% of succinic acid contained in the initial process solution, while 23% of sodium sulfate was contained in the filtrated solution and was removed. Further, in the recovered crystal of succinic acid, Na was completely removed, and furthermore, other impurities were removed by 97%

(Re-Crystallization)

In order to remove other components contained in the recovered crystal by the Low Temperature Crystallization, 59 g of the crystal recovered by the Low Temperature Crystallization was added to 200 g of water in an Erlenmeyer flask with a stopper with stirring. Then, the flask was plugged with a stopper, and the solution in the flask was warmed with stirring in a water bath at 65° C. in the hermetically closed state.

Warming at 65° C. and stirring by a stirrer were continued, and when it was confirmed that the crystals were completely dissolved, 2.5 g of activated carbons BA-50 (manufactured by Ajinomoto-Fine-Techno Co., Inc.), 5% relative to the weight of succinic acid, was added. The treatment by warming at 65° C. and the stirring was continued for 1 hour after adding the activated carbons, and then the filtrated solution was recovered by a suction filtration using a 5C filter paper and a Nutsche funnel having an inner diameter of 110 mm which was warmed at 65° C. in advance. The weight of the recovered filtrated solution was 235 g, and 47 g of succinic acid was contained in it.

All of the recovered filtrated solution was transferred into an Erlenmeyer flask with a stopper, and the solution in the flask was cooled with stirring in a water bath at 50° C. in the hermetically closed state. After the filtrated solution was stirred with maintaining the temperature at 5° C. for 2 hours, solid-liquid separation was performed by a suction filtration using a 5B filter paper and a Nutsche funnel having an inner diameter of 110 mm which was kept at 5° C. in advance. Further, after all of the crystals were recovered on the funnel, the crystals on the funnel were rinsed by charging 50 g of water with a temperature of 5° C.

The weight of the recovered crystal was 42 g, containing 38 g of succinic acid, 0 g of sodium sulfate, 4 g of water, and 0 g of other components. Also, the weight of the recovered filtrated solution including the rinse water was 243 g in total, containing 9 g of succinic acid, 0 g of sodium sulfate, 233 g of water, and 2 g of other components. By re-crystallization, 53% of succinic acid was recovered as the crystal relative to 100% of succinic acid contained in the initial process solution. In addition, impurities were completely removed from the recovered crystal of succinic acid. When the filtrated solutions recovered in the processes of the Low Temperature Crystallization and the re-crystallization were recycled to the subsequent treatments, the amount of the loss of succinic acid that cannot be recycled in the present Example was 11 g, 15% relative to its content in the initial process solution.

Example 4

The Second Separation and Purification of the Reaction Solution (B)

(Addition of Sulfuric Acid)

To 2060 g (2.0 L) of the reaction solution (B) having the composition shown in Table 1, 168 g of concentrated sulfuric acid was added with stirring. As the result, the obtained solution contained 2228 g (2.1 L) of the initial process solution, containing 161 g (9.3 g/100 g-water) of succinic acid and 244 g (14.0 g/100 g-water) of sodium sulfate.

(Recycle of the Filtrated Solution)

To the obtained solution with sulfuric acid, 604 g of the filtrated solution recovered at the process of Low Temperature Crystallization and 563 g of the filtrated solution recovered at the process of re-crystallization in Example 2 were added and mixed to prepare the initial process solution. The obtained initial process solution contained 3395 g (3.3 L) of the mixture solution, containing 219 g (7.9 g/100 g-water) of succinic acid and 302 g (10.9 g/100 g-water) of sodium sulfate.

(High Temperature Crystallization)

Subsequently, the initial process solution was concentrated with a rotary evaporator to be 1019 g to make the concentration of succinic acid 49 g/100 g-water and sodium sulfate 67 g/100 g-water, and then all of the solution was transferred into an Erlenmeyer flask with a stopper. The flask was plugged with a stopper and then the solution in the flask was warmed with stirring in a water bath at 80° C. in the hermetically closed state. After the concentrated solution was stirred at 80° C. for 2 hours, solid-liquid separation was performed by a suction filtration using a 5B filter paper and a Nutsche funnel having an inner diameter of 110 mm which was warmed at 80° C. in advance.

The weight of recovered filtrated solution was 743 g, containing 202 g of succinic acid, 73 g of sodium sulfate, 430 g of water, and 39 g of other components. Also, the weight of the recovered crystal was 275 g, containing 230 g of sodium sulfate, 18 g of succinic acid, 20 g of water, and 8 g of other components. By the High Temperature Crystallization, 92% of succinic acid in the initial process solution was recovered in the filtrated solution, and 76% of sodium sulfate was removed as the crystal.

(Low Temperature Crystallization)

All of 743 g of the filtrated solution recovered by the High Temperature Crystallization was transferred into an Erlenmeyer flask with a stopper. The flask was plugged with a stopper and then the solution in the flask was cooled with stirring in a water bath at 35° C. in the hermetically closed state. After the concentrated solution was stirred at 35° C. for 2 hours, solid-liquid separation was performed by a suction filtration using a 5B filter paper and a Nutsche funnel having an inner diameter of 110 mm which was kept at 35° C. in advance. Further, after all of the crystals were recovered on the funnel, the crystals on the funnel were rinsed by charging 202 g of water with a temperature of 35° C.

The weight of the recovered crystal was 174 g, containing 156 g of succinic acid, 0 g of sodium sulfate, 14 g of water, and 4 g of other components. Also, the weight of the recovered filtrated solution including the rinse water was 772 g in total, containing 46 g of succinic acid, 73 g of sodium sulfate, 618 g of water, and 35 g of other components. By the Low Temperature Crystallization, 71% of succinic acid was recovered as the crystal relative to 100% of succinic acid contained in the initial process solution, while 24% of sodium sulfate was contained in the filtrated solution and was removed. In addition, in the recovered succinic acid crystal, Na was completely removed, and furthermore other impurities were removed by 96%.

(Re-Crystallization)

In order to remove other components contained in the recovered crystal by the Low Temperature Crystallization, 174 g of the crystal recovered by the Low Temperature Crystallization was added to 650 g of water in an Erlenmeyer flask with a stopper with stirring. Then, the flask was plugged with a stopper, and the solution in the flask was warmed with stirring in a water bath at 65° C. in the hermetically closed state.

Warming at 65° C. and stirring by a stirrer were continued, and when it was confirmed that the crystals were completely dissolved, 4.7 g of activated carbons BA-50 (manufactured by Ajinomoto-Fine-Techno Co., Inc.), 3% relative to the weight of succinic acid, was added. The treatment by warming at 65° C. and stirring was continued for 1 hour after adding the activated carbons, and then the filtrated solution was recovered by a suction filtration using a 5C filter paper and a Nutsche funnel having an inner diameter of 110 mm which was kept at 5° C. in advance. Further, after all of the crystals were recovered on the funnel, the crystals on the funnel were rinsed by charging 150 g of water with a temperature of 5° C.

The weight of the recovered crystal was 137 g, containing 125 g of succinic acid, 0 g of sodium sulfate, 12 g of water, and 0 g of other components. Also, the weight of the recovered filtrated solution including the rinse water was 798 g in total, containing 25 g of succinic acid, 0 g of sodium sulfate, 771 g of water, and 2 g of other components. By re-crystallization, 57% of succinic acid was recovered as the crystal relative to 100% of succinic acid contained in the initial process solution. In addition, impurities were completely removed from the recovered crystal of succinic acid. When the filtrated solutions recovered in the processes of the Low Temperature Crystallization and the re-crystallization were recycled to the subsequent treatments, the amount of the loss of succinic acid that cannot be recycled in the present Example was 24 g, 11% relative to its content in the initial process solution.

TABLE 1

|  | Reaction solution (A) | | | Reaction solution (B) | | | Reaction solution (C) | | |
| --- | --- | --- | --- | --- | --- | --- | --- | --- | --- |
|  | (g/L) | (meq/L) | (g/100 g-water) | (g/L) | (meq/L) | (g/100 g-water) | (g/L) | (meq/L) | (g/100 g-water) |
| Succinic acid | 116 | 1959 | 14.4 | 81 | 1368 | 9.6 | 36 | 613 | 4.0 |
| Na | 52 | 2274 | 6.5 | 39 | 1717 | 4.7 | 24 | 1023 | 2.6 |
| Alkali metals other than Na | 0 | 0 | 0 | 0 | 0 | 0 | 0 | 0 | 0 |
| Other components*[1] | 31 | — | 3.9 | 39 | — | 4.6 | 46 | — | 5.1 |

*[1] In other components were contained organic acids such as acetic acid, lactic acid, pyruvic acid, phthalic acid and the like, glucose, phosphoric acid, trace metals and the like.

TABLE 2

|  |  | Solution (A) | | | Solution (B) | | | Solution (C) | | |
| --- | --- | --- | --- | --- | --- | --- | --- | --- | --- | --- |
|  |  | (g) | (meq) | (g/100 g-water) | (g) | (meq) | (g/100 g-water) | (g) | (meq) | (g/100 g-water) |
| Before adding sulfuric acid | Amount of reaction solution | 2080 |  |  | 2060 |  |  | 2040 |  |  |
|  | Water | 1682 |  |  | 1742 |  |  | 1829 |  |  |
|  | Succinic acid | 231 | 3919 | 13.7 | 161 | 2735 | 9.3 | 72 | 1226 | 4.0 |
|  | Na | 105 | 4548 | 6.2 | 79 | 3433 | 4.5 | 47 | 2046 | 2.6 |
| Amount of sulfuric acid added |  | 223 | 4548 |  | 168 | 3433 |  | 100 | 2046 |  |
| After adding sulfuric acid | Amount of reaction solution | 2303 |  |  | 2228 |  |  | 2140 |  |  |
|  | Succinic acid | 231 | 3919 | 13.7 | 161 | 2735 | 9.3 | 72 | 1226 | 4.0 |
|  | Sodium sulfate | 323 | 4548 | 19.2 | 244 | 3433 | 14.0 | 145 | 2046 | 7.9 | was kept at 65° C. in advance. The weight of the recovered filtrated solution was 785 g, and 150 g of succinic acid was contained in it.

All of the recovered filtrated solution was transferred into an Erlenmeyer flask with a stopper, and the solution in the flask was cooled with stirring in a water bath at 50° C. in the hermetically closed state. After the filtrated solution was stirred with maintaining the temperature at 5° C. for 2 hours, solid-liquid separation was performed by a suction filtration using a 5B filter paper and a Nutsche funnel having an inner

The invention claimed is:

1. A process for producing succinic acid, comprising (1) a step to add sulfuric acid into a solution containing an alkali metal succinate, (2) a step to precipitate and remove the crystal of an alkali metal sulfate from the solution, and (3) a step to precipitate and recover the crystal of succinic acid.

2. The process for producing succinic acid according to claim 1, wherein an amount of sulfuric acid to be added in the step (1) corresponds to the equivalent amount of the alkali metal contained in the solution.

3. The process for producing succinic acid according to claim 1, wherein the removal of a crystal of the alkali metal sulfate in the step (2) is performed by a solid-liquid separation in a state that the crystal of alkali metal sulfate is precipitated by concentrating and heating the solution that is obtained by adding sulfuric acid in the step (1) and succinic acid is dissolved in the solution.

4. The process for producing succinic acid according to claim 3, wherein the concentration of the alkali metal sulfate salt is 20 g/100 g-water or more and the concentration of succinic acid is 60 g/100 g-water or less in the solution that is obtained by concentrating and heating the reaction solution added with sulfuric acid, and temperature of heating is 50° C. or higher.

5. The process for producing succinic acid according to claim 1, wherein the recovery of the crystal of succinic acid in the step (3) is performed by a solid-liquid separation in a state that the crystal of succinic acid is crystallized by cooling the solution that is obtained after removing the crystal of the alkali metal sulfate, and the unremoved alkali metal sulfate that is remained in the step (2) is dissolved in the solution.

6. The process for producing succinic acid according to claim 5, wherein the cooling temperature of the solution that is obtained after removing the crystal of the alkali metal sulfate is 50° C. or lower.

7. The process for producing succinic acid according to claim 5, further comprising a step to rinse the recovered crystal of succinic acid by water, the temperature of which is lower than the temperature employed for cooling of the solution that is obtained after removing the alkali metal sulfate.

8. The process for producing succinic acid according to claim 5, further comprising a step in which the recovered crystal of succinic acid is re-dissolved into water, then succinic acid is re-crystallized by cooling the resulting solution and recovered.

9. The process for producing succinic acid according to claim 8, further comprising a step to treat the solution containing the re-dissolved crystal of succinic acid with activated carbons after the re-dissolution of the crystal of succinic acid into water and before the recovery of succinic acid by re-crystallization.

10. The process for producing succinic acid according to claim 3, wherein the remaining solution after recovering the crystal of succinic acid is reprocessed by mixing it with the solution before the concentration and heating in the step (2).

11. The process for producing succinic acid according to claim 3, wherein the rinse water recovered after rinsing the recovered crystal of succinic acid is reprocessed by mixing it with the solution before the concentration and heating in the step (2).

12. The process for producing succinic acid according to claim 1, wherein the solution containing the alkali metal succinate is a broth by microorganisms.

13. The process for producing succinic acid according to claim 1, wherein the solvent of the solution that contains the alkali metal succinate is water.

* * * * *